US006239255B1

(12) United States Patent
Furlong et al.

(10) Patent No.: US 6,239,255 B1
(45) Date of Patent: *May 29, 2001

(54) VERSATILE SURFACE PLASMON RESONANCE BIOSENSORS

(76) Inventors: Clement E. Furlong, 15705 Point Monroe Dr. NE., Bainbridge Island, WA (US) 98110; Richard Woodbury, 5405 NE. 194th Pl., Seattle, WA (US) 98155

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/920,427
(22) Filed: Aug. 29, 1997
(51) Int. Cl.7 ..................................... C07K 7/08
(52) U.S. Cl. .................. 530/327; 530/345; 530/350; 530/402; 435/287.1; 435/287.9; 435/288.7
(58) Field of Search .................... 530/345, 324, 530/327, 350, 402; 435/287.1, 287.9, 288.7

(56) References Cited

PUBLICATIONS

Brown, S. 'Metal Recognition by Repeating Polypeptides', Nature of Biotechnology, vol. 15, pp. 269–272, Mar. 1997.*
Wang et al. 'Simplified Purification and Testing of Colloidal Gold Probes', Biochemistry, vol. 85, pp. 109–115, 1985.*
Ackerman et al. 'Differential Surface Labeling and Internalizatio of Glugagon by Peripheral Leukocytes', Journal of Histochemistry and Cytochemistry, vol. 31, No. 3, pp. 433–440, 1983.*

Wohlheuter et al. 'Analysis of Binding of Monoclonal Antibody to Malarial Peptide by Surface Plasmon Resonace Biosensor and Integrated Rate Equation', Journal of Immunology. vol. 153, No. 1–2. pp. 181–189, Jul. 1994.*

Altschuh et al. 'Determination of Kinetic Constants for the Interaction Between a Monoclonal Antibody and Peptide Using Surface Plasmon Resonance', Biochemistry. vol. 31, pp. 5298–6304, 1992.*

(List continued on next page.)

Primary Examiner—Christopher S. F. Low
Assistant Examiner—Anish Gupta
(74) Attorney, Agent, or Firm—Sanford E. Warren, Jr.; Edwin S. Flores; Gardere Wynne Sewell LLP

(57) ABSTRACT

A method of binding a recognition element to a gold surface (24) comprising the steps of attaching a GBP-AP protein (10) to a gold surface (24), digesting away the AP domain of the protein (10) with a proteolytic enzyme from the bound GBP domain (12) attached to the gold surface (24), and attaching a recognition element, such as Protein A (52) or an antibody 72, antigen, nucleic acid or other binding partner to the GBP domain (12) which remains on the gold surface (24), is disclosed.

19 Claims, 4 Drawing Sheets

OTHER PUBLICATIONS

Khilko et al. 'Direct Detection of Major Histocompatibility Complex Class I Binding To Antigenic Petides Using Surface Plamon Resonance', Journal of Biological Chemistry. vol. 268, No. 21. pp. 15425–15434, Jul. 1993.*

File Caplus on STN. No. 1988:34542. Hiemstra et al. 'Distribution of Newly Synthesized Lipoprotein Ove the Outer Membran and the Peptidoglycan Sacculu of an *Escherichia coli LAC–LPP* Strain', J. Bacteriology. vol. 169, No. 12, pp 5434–44. (abstract only), 1988.*

File Medline on STN. No. 88166770. Taatjes et al. 'Streptococcal Protein G–Gold Complex: Comparison with Staphycococcal Protein A–Gold Complex for Spot Blotting and Immunolabeling', European J. of Cell Biology. vol. 45, No. 1, pp. 151–159, Dec. 1987.*

Analysis of Binding of Monoclonal Antibody to a Malarial Peptide by Surface Plasmon Resonance Biosensor and Integrated Rate Equations, Journal of Immunology, Jul. 1994.

Real–Time Competitive Kinetic Analysis of Interactions between Low–Molecular–Weight Ligands in Solution and Surface–Immobilized Receptors, Analytical Biochemistry by Academic Press, Inc., 1997.

Temperature Dependence of Magnetic Receptibility for $RbVCl_3$ (dehydrated), Chemical Communications, 1968.

Formation of Monolayer Films by the Spontaneous Assembly of Organic Thiols from Solution onto Gold, Journal of American Cemical Society, 1989.

Enhancement by N–Hydroxysulfosuccinimide of Water–Soluble Carbodiimide–Mediated Coupling Reactions, Analytical Biochemistry, 1986.

Differential Surface Labeling and Internalization of Glucagon by Peripheral Leukocytes, Journal of Histochemistry and Cytochemistry, 1983.

Metal–recognition by repeating polypeptides, Nature Biotechnology, 1997.

Simplified Purification and Testing of Colloidal Gold Probes, Histochemistry, 1985.

Peptides in Tetanus Toxin Production, Journal of Biological Chemistry, Nov.–Dec. 1956.

* cited by examiner

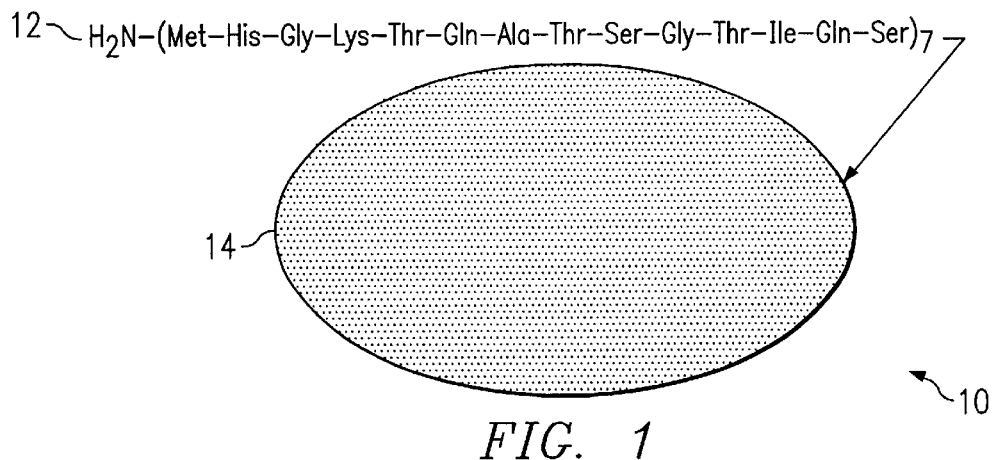
FIG. 1
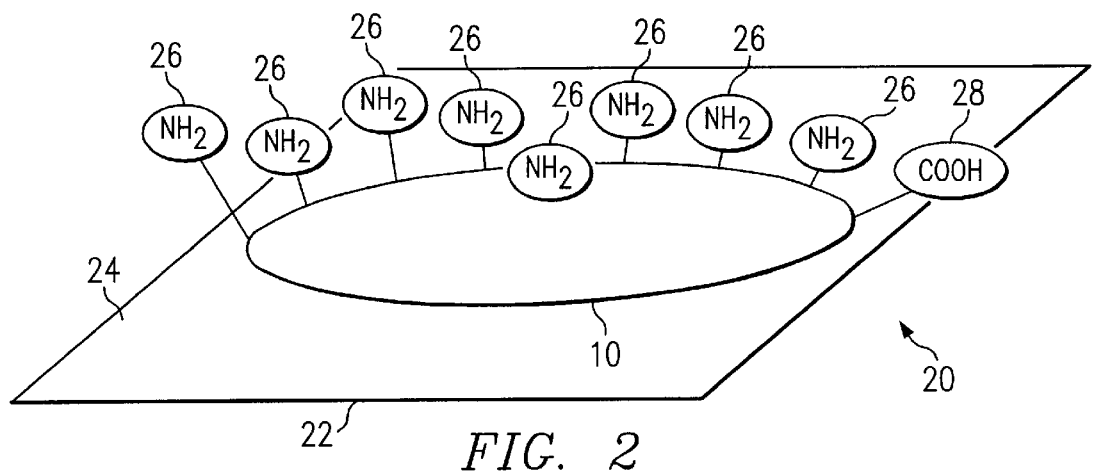
FIG. 2
FIG. 4
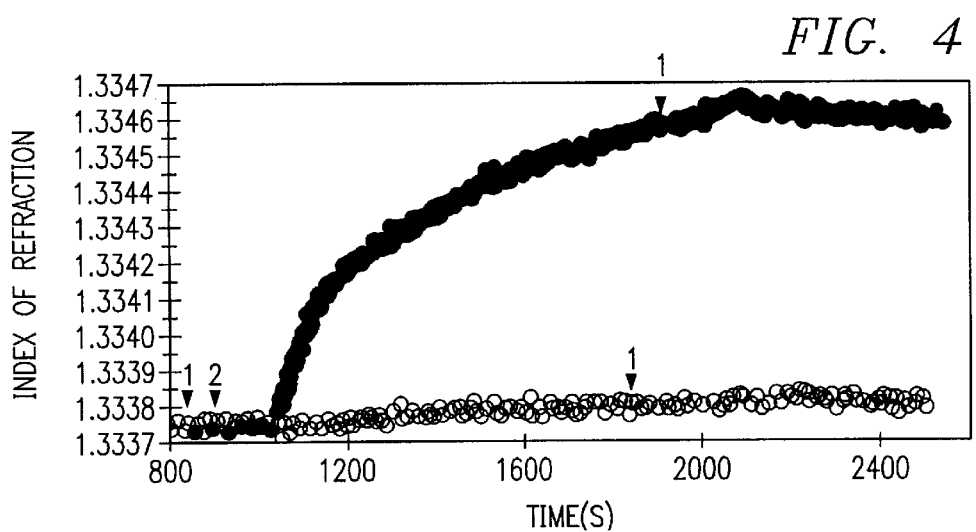

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 14
      (B) TYPE: amino acid
      (C) STRANDEDNESS: single
      (D) TOPOLOGY: linear

```
    (ix) SEQUENCE DESCRIPTION: SEQ ID NO: 1:

Met His Gly Lys Thr Gln Ala Thr Ser Gly Thr Ile Gln Ser
1               5                   10
```

VERSATILE SURFACE PLASMON RESONANCE BIOSENSORS

TECHNICAL FIELD OF THE INVENTION

The present invention relates in general to the field of biosensors, more particularly, the present invention is directed to a surface plasmon resonance (SPR) miniature integrated sensor using a gold-binding repeating polypeptide to which variable recognition elements are attached at the sensor surface.

BACKGROUND OF THE INVENTION

Without limiting the scope of the invention, its background is described in connection with surface plasmon resonance sensors, as an example.

Heretofore, in this field, the development of sensors for the detection of specific molecules within specimens or samples have required expensive equipment, highly trained personnel, large samples, and days to weeks to complete. While the detection of contaminants has been an active area of research, present systems are limited in the range of applications and are unable to detect specific compounds in real-time. Present systems for the analysis of specific binding phenomena have included antibody-antigen complex formation and receptor-ligand interactions for the detection of small molecules.

An active area of sensor development has been the use of an optical phenomenon known as surface plasmon resonance (SPR). Biosensors of this type, such as the BIAcore line from Biacore, Upsala, Sweden, are available for use in research and development. Two factors limiting the general use of SPR biosensors, however, are the relatively high cost of developing and using specific biosensors and the lack of mobility for field analysis.

The most difficult step in producing a surface plasmon resonance biosensor is the attachment of specific recognition elements to the gold surface of the sensor. The problems associated with attaching organic molecules to gold are manifold. One problem is the need to highly purify the specific recognition elements so as to avoid non-specific surface interactions by impurities in the preparation. Another problem is the difficulty in stably attaching the specific recognition element to a metal. Yet another problem is the need to prepare and treat the gold surface to prevent Non-Specific Binding ("NSB").

The recognition elements of current SPR biosensor are attached to a gold sensor surface by forming a monolayer of long-chain alkanethiols with suitable reactive groups on one end of the molecule and a gold-complexing thiol on the other. The actual molecular recognition elements are attached directly to the alkanethiol monolayer or to a hydrogel layer. An example of hydrogel monolayer is carboxymethyl dextran, that is attached to the monolayer.

The purpose of providing an additional hydrogel layer over the alkanethiol monolayer is to favor normal protein interaction and function, which are disrupted by the thiol groups used for attaching proteins. The additional monolayer is also necessary to provide a more hydrophilic environment at the gold surface than is provided by the monolayer alone. The presence of a hydrogel is also necessary to reduce the non-specific binding of proteins on the gold surface and to stabilize the alkanethiol monolayer attachment to gold.

Under relatively stable and controlled conditions in the laboratory, the gold-sulfur association is relatively stable. Outside the laboratory, however, the association of molecules necessary to obtain a surface plasmon resonance reading are more unpredictable and less reliable. The decreased reliability is due in part to the presence of oxidants, other sulfur-containing compounds and acidic solutions, all of which limit the practical use of SPR biosensors constructed with alkanethiol monolayers. Consequently, present SPR biosensors have failed to approach their full potential of applications.

Brown recently cloned a novel Gold-Binding Protein ("GBP") and characterized the specific recognition element. Stanley Brown, *Metal Recognition by Repeating Polypeptides*, Nature Biotechnology, Vol. 15, March 1997. He suggested that the GBP could be genetically engineered as a fusion protein with specific recognition elements for use in constructing biosensors. Brown did not, however, disclose a method of using a GBP to construct surface plasmon biosensors directed to a specific molecule or molecules. Nor does Brown discuss a method of employing protein-coupling chemistry to create chimeric proteins consisting of the GBP and several different recognition elements. Furthermore, Brown failed to disclose a method of using and making a biosensor using a GBP.

What is needed is a low cost, mobile sensor with more stable recognition elements. Also needed is an apparatus and method that enables the developer and user of Surface Plasmon Resonance-based biosensors ("SPR-biosensors") to easily and reliably construct, evaluate, produce and use SPR-biosensors with specific recognition elements that attach to the gold surface.

SUMMARY OF THE INVENTION

The present invention disclosed herein comprises a method of producing a stable surface plasmon biosensor. More particulary, the present invention is directed to a method of improving the strength and stability of the molecular bonds between the gold surface of a surface plasmon resonance biosensor and the specific recognition element of the biosensor. The present invention is a method for immobilizing a molecule on a gold surface comprising, attaching a gold binding peptide to the gold surface and attaching the molecule to the gold binding peptide.

More particularly, the present invention is directed to a method of immobilizing a molecule on a gold surface in which the gold binding peptide is a naturally occurring polypeptide structure. Alternatively, the gold binding peptide may be a genetically engineered or synthetically constructed polypeptide structure. Even more particularly, the genetically engineered or synthetically constructed repeated polypeptide structure is the repeated amino acid sequence MHGKTQATSGTIQS (SEQ ID NO.: 1).

The present invention also encompasses a method of binding a recognition element to a gold surface comprising the steps of, attaching a Gold Binding Peptide-Alkaline Phosphotase chimera ("GBP-AP") protein to the gold surface, digesting away the alkaline phosphatase domain of the protein with proteolytic enzymes leaving the GBP domain bound to the gold surface, and attaching a recognition element to the GBP domain. In one embodiment the proteolytic enzyme used for digesting away the alkaline phosphatase domain is trypsin. The method of the present invention may further comprise the step of cross linking the bound GBP domain to adjacent molecules.

Yet another embodiment of the present invention is a molecular specificity structure comprising, a gold surface, a gold binding peptide foundation layer coating the gold surface, and a sensing layer attached to said gold binding peptide layer, wherein the sensing layer is immobilized about the gold surface, the sensing layer having the characteristic quality of binding to a specific target analyte. The specificity structure may be further defined as comprising a specific recognition element, which may be for example, an antibody, a lectin, a hormone receptor, a nucleic acid, a carbohydrate, a lipid, or any antigen, hormone or other binding partner. The specificity layer of the present invention may be further defined as comprising an intermediary adaptive layer capable of reversibly binding a plurality of recognition elements with different specificities, and a specific recognition element bound to the intermediary adaptive layer.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 shows a drawing of the gold-binding peptide chimera of the present invention;

FIG. 2 is a drawing of a gold-binding peptide chimera attached to the gold-plated surface following treatment with trypsin for use with the present invention;

FIG. 4 shows the SPR signal generated during the binding of mouse monoclonal anti-fluorescyl antibodies to fluorescyl-labeled GBP on a biosensor used in one embodiment of the present invention;

DETAILED DESCRIPTION OF THE INVENTION

Figure 3:
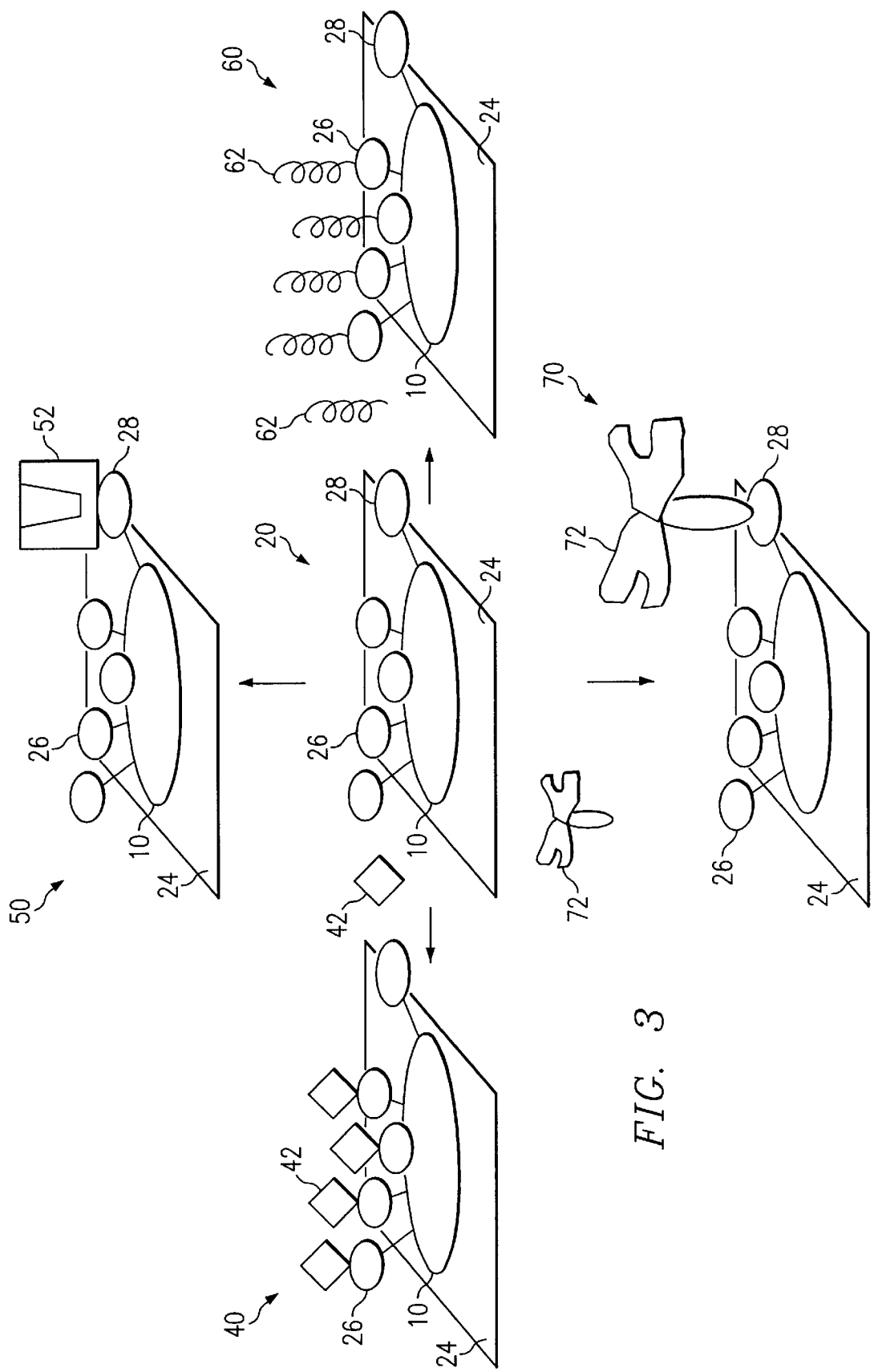
FIG. 3 is a drawing of alternative configurations for the attachment of specific recognition elements to the surface of a gold-plated cell.

While the making and using of various embodiments of the present invention are discussed in detail below, it should be appreciated that the present invention provides many applicable inventive concepts which can be embodied in a wide variety of specific contexts. Specifically it is anticipated that the use of binding techniques, as disclosed herein, will have utility with biosensing applications, including biosensing devices such as, surface plasmon resonance ("SPR"), light transmission, wave-guide and chemiluminescence sensors. The specific embodiments discussed herein are merely illustrative of specific ways to make and use the invention and do not delimit the scope of the invention.

The present invention uses a Gold-Binding Polypeptide ("GBP") with miniature SPR devices to construct biosensors that are stable, sensitive, selective and capable of delivering reproducible measurements. The miniature SPR-GBP devices of the present invention takes advantage of the trypsin insensitivity of the gold binding peptide domain where it is bound to gold to provide a gold binding molecule that can be engineered to provide a simple way of introducing specific recognition elements to the gold surfaces of SPR biosensors. More importantly, the total time required to construct the biosensor as disclosed herein, was 5 to 6 hours. Fusion proteins containing gold-binding polypeptide and desired recognition elements can also be used with the present invention as described in detail herein.

For many recognition elements of interest, production as fusion proteins by genetic engineering may not be feasible or desirable. Even when functional recognition elements can be fused with the GBP and produced by genetic engineering methods, each chimeric protein is likely to have unique problems associated with its production, stability or purification. The chemical methods described herein, allow those of skill in the art to practice the present invention. The apparatus and method of the present invention provides a useful and direct approach to quickly constructing, evaluating, producing and implementing the use of GBP-based SPR biosensor.

A wide variety of specific molecules may be used to direct the specific interactions of the biosensor. For example, the ligand may be an antigen and the specific recognition element can be an antibody to the antigen. The invention is not to be taken as limited to assays of antibodies or antigens, however, examples of ligands that may be analyzed by the method of the present invention are given in Table 1 below, together with an indication of a suitable specific binding partner in each instance.

TABLE 1

| Ligand | Specific Recognition Element |
| --- | --- |
| antigen | specific immunoglobulin |
| immunoglobulin | antigen |
| hormone | hormone receptor |
| hormone receptor | hormone |
| polynucleotide strand | complementary polynucleotide strand |
| avidin | biotin |
| biotin | avidin |
| protein A | immunoglobulins |
| protein G | IgG immunoglobulins |
| immunoglobulin | Protein A or Protein G |
| enzyme or inhibitor | enzyme cofactor (substrate) |
| enzyme cofactor or inhibitor | enzyme (substrate) |
| lectins | specific carbohydrate |
| specific carbohydrate | lectins |

The GBP-based SPR biosensor of the invention has broad applicability but in particular may be used to assay: hormones, including peptide hormones (e.g. thyroid stimulating hormone (TSH), luteinizing hormone (LH), human chorionic gonadotropin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxins, vitamins, viruses such as influenza, parainfluenza, adeno-, hepatitis, respiratory and AIDS viruses, or microorganisms or cardiac markers (e.g. creatine kinase, myoglobin, troponin I, troponin T).

It will be understood the term "antibody" as used herein includes within its scope:

(a) any of the various classes or sub-classes of immunoglobulin, e.g. IgG, IgA, IgM, or IgE derived from any of the animals conventionally or unconventionally used as a source of sera, e.g. sheep, rabbits, goats or mice to name a few;

(b) monoclonal antibodies whether produced by cell fusion with immortalized cells, by recombinant techniques in eukaryotic or prokaryotic cells;

(c) intact molecules or "fragments" of antibodies, monoclonal or polyclonal, the fragments being those which contain the binding region of the antibody, i.e. fragments devoid of the Fc portion (e.g. Fab, Fab', F(ab')$_2$) or fragments obtained by reductive cleavage of the disulphide bonds connecting the heavy chain components in the intact antibody so long as they retain antigen binding capabilities.

Methods for the preparation of fragments of antibodies, chimeric antibodies, polyvalent antibodies, bivalent antibodies, and the like are well known in the art and will not be described herein.

The term "antigen" as used herein will be understood to include both naturally antigenic species (for example, proteins, bacteria, bacterial fragments, cells, cell fragments, carbohydrates, nucleic acids, lipids, and viruses, to name a few) and haptens which may be rendered antigenic under suitable conditions and recognized by antibodies or antibody fragments.

The present invention provides a sensor for detecting a ligand in a sample by a method described hereinbefore which comprises an optical structure having a substrate coated with a thin layer of metal, which metal layer is itself coated with a layer of GBP employed when the sensor is in use and which GBP layer carries a specific binding partner for the ligand it is desired to detect.

FIG. 1 shows the structure of the gold-binding peptide carrier protein chimera 10 of the present invention. The peptide 12, has a gold-binding motif, MHGKTQATSGTIQS (SEQ ID NO.: 1) that is depicted in FIG. 1 as having seven repeats. More or less repeats may be necessary depending on the extend of gold-binding necessary and the characteristics of the protein. The peptide is attached to a carrier 14. The carrier 14 may be, for example, a polypeptide or protein that is easily expressed, isolated or that exhibits enzymatic activity, such as alkaline phosphatase, β-galactosidase. Alternatively, the gold binding peptide 12 may be chemically attached to the carrier 14. Alternative gold binding domains may be used as the peptide 12 with the apparatus and methods of the present invention.

More specifically, the present invention is a gold-binding peptide surface plasmon resonance biosensor cell (GBP-SPRB) that is schematically depicted in FIG. 2 and is generally numbered 20. The GBP-SPRB 20 of the present invention includes a cell or plate 22 on which a gold surface 24 has been disposed. A gold-binding peptide carrier chimera 10, having multiple amino groups 26 and a carboxy end 28 is depicted attached to gold surface 24.

The apparatus and method of the present invention provides a low cost, SPR sensor that is durable and versatile. In one embodiment of the present invention a miniaturized SPR biosensor has the following dimensions: 4 cm×3 cm×1 cm. Other dimensions, however, may be substituted as is well known to those of skill in the art of SPR sensors.

FIG. 3 depicts alternative embodiments of GBP-SPRB 20 of the present invention having alternative specific recognition elements. In the center of FIG. 3 is depicted the GBP-SPRB 20 having disposed thereon a gold-binding peptide 10, having multiple amino groups 26 and a carboxy end 28 is depicted attached to gold surface 24. In the embodiment depicted as 40, the GBP-SPRB 20 has fluorescein-hapten molecules 42 attached to the amino groups 26 of the gold-binding peptide 10.

In the embodiment of the GBP-SPRB designated 50 at the top of FIG. 3 is a gold-binding peptide 10 to which protein A 52 has been conjugated via the carboxy end of the gold-binding peptide 10. In the embodiment of the GBP-SPRB 60 depicted on the right hand side of GBP-SPRB 20, a target peptide 62 is attached to the amino groups 26 of the gold-binding peptide 10. Alternatively, as depicted in the bottom of FIG. 3, a GBP-SPRB 70 is depicted to which an antibody 72 has been attached via the carboxy end 28 of the gold-binding peptide 10.

The biosensor of the present invention can be fitted with a flow cell. The present invention uses a SPR biosensor coupled to a gold-binding polypeptide to construct a durable and reliable biosensor. The following example demonstrates that one embodiment of the present invention is a selective, low cost, durable and highly mobile biosensor that has wide-spread clinical, industrial, and environmental applications.

I. Plasmid Construct

An *E. coli* cell line expressing the plasmid pSB3053 was used to produce a chimeric protein consisting of a unique gold-binding polypeptide (GBP) with seven repeats of the amino acid sequence MHGKTQATSGTIQS (SEQ ID NO:1) and alkaline phosphatase (GBP-AP). See *Brown*, 1997. As a control, another cell line containing an AP expression vector, pSB2991, with no polypeptide insert was expressed in parallel. By attaching AP to the gold-binding polypeptide (GBP-AP) association of the GBP to gold can be monitored to measure AP enzymatic activity.

II. Attachment of Recognition Elements to the GBP on Gold

The GBP can be genetically engineered as a fusion protein with specific recognition elements for use in constructing biosensors. In operation, a simple protein-coupling chemistry was used to create chimeric proteins consisting of the GBP and several different recognition elements. As a first step, it was determined whether or not trypsin could cleave the GBP-AP between its two functional domains while the GBP-AP was bound to gold. The interaction of the GBP domain with gold might protect it from extensive proteolysis and possibly the GBP would remain on the gold, thereby providing potentially reactive groups to which specific recognition elements could be covalently attached.

Table 2 shows the results of the trypsin cleavage analysis and indicates that cleavage of GBP-AP by trypsin released enzymatically active AP into solution. The GBP remained attached to the gold as indicated indirectly by the inability of added intact GBP-AP to bind in significant levels to the derivatized gold. In the absence of gold, the proteolysis of GBP-AP by trypsin was extensive because the cleavage products were unable to block the binding of intact GBP-AP to gold. The protease-treated GBP on gold provided a substrate to which other proteins such as alkaline phosphatase, antibodies or protein A 52 were attached following activation of the carboxyl group(s) in the GBP by reaction with carbodiimide. Further, the amino groups of the GBP bound to gold were derivatized with fluorescyl groups by reaction with fluorescein isothiocyanate. The reconstructed adduct of the GBP and AP on gold was highly resistant to cleavage by trypsin, retaining 90% of the AP activity on gold after 2 hours of digestion.

TABLE 2

Proteolysis of the GBP-AP bound to gold powder with bovine trypsin.

| | Study I O.D. units - 405 nm | | | Study II O.D. units - 405 nm | | |
|---|---|---|---|---|---|---|
| Sample | Incubation time (min) | Au pellet | Incubation supernatant fluid | Incubation time (min) | Au pellet | Incubation supernatant fluid |
| 1- No trypsin | 60 | 0.57 | 0.01 | 120 | −2.0 | 0.16 |
| 2- Trypsin added | 5 | 0.33 | 0.26 | 5 | 1.8 | 0.27 |
| 3- Trypsin added | 10 | 0.32 | 0.34 | 15 | 1.1 | 0.35 |
| 4- Trypsin added | 1S | 0.28 | 0.39 | 30 | 0.7 | 0.39 |
| 5- Trypsin added | 30 | 0.210 | 0.50 | 60 | 0.5 | 0.47 |
| 6- Trypsin added | 60 | 0.129 | 0.34 | 120 | 0.3 | 0.47 |

In the first study 10 mg of Au powder placed in each of six microfuge tubes was rinsed once in PKT buffer and incubated in 1 ml of 2 μg of GBP-AP in PKT buffer for 1 hour at room temperature. The gold powder was collected by centrifugation and rinsed twice in 1 ml of PKT buffer. Incubation of the GBP-AP on gold in the absence or presence of trypsin was done at room temperature by the addition of 1 ml of TB or of 1 ml of 100 ng of trypsin in TB. After the appropriate incubation time the Au powder pellets and supernatant fluids were collected by centrifugation. The Au powder pellets were assayed for AP activity by adding 1 ml of AP substrate at pH 8.0 to the pellet, mixing the contents and recording the absorbances at 405 nm after 15 min. AP activities in the supernatant fluid fractions were assayed by mixing a 100 ul aliquot of each in 900 ul of AP substrate solution and the absorbances at 405 ul aliquot of each in 900 ul of AP substrate solution and the absorbances at 405 nm were recorded after 15 min.

In the second study, the procedure followed was the same as described hereinabove, with the exception that for each sample 30 mg of gold powder was incubated with 6 ug of GBP-AP, the trypsin concentration was increased to 500 ng per ml of buffer and the last time point was at 120 min.

III. Fluorescyl-labeled GBP on Gold Biosensor

A biosensor for detecting specific antibodies was constructed with an SPR minisensor and GBP-AP obtained from the osmotic shock fluid lysate of a GBP-AP expressing *E. coli* containing the pSB3053 plasmid. Following by trypsin cleavage, fluorescyl groups were attached to residual GBP attached to gold on the surface of the minisensor in a reaction with fluorescein isothiocyanate. The fluorescyl groups provided an antigenic target to bind the anti-fluorescyl monoclonal antibody 72, (4.4.20). This biosensor functioned selectively, as expected, by responding to antibody 72, (4.4.20) in ascites fluid but not to control antibodies. A biosensor prepared in the above manner was used daily for 4 weeks with little decrease in response even after more than 40 regenerations of the recognition element in 0.1 M Glycine-HCl buffer, pH 2.1.

The functionality of this biosensor may not have been due solely to the presence of fluorescyl-labeled-GBP because the sensor also was exposed to other proteins in the osmotic shock fluid and calf serum. To eliminate the possibility that proteins other than the GBP contributed to the biosensor's function, a second biosensor was constructed using immunopurified GBP-AP from osmotic shock fluid. The GBP-AP was purified on a immobilized rabbit anti-alkaline phosphatase antibody column. During the construction of the biosensor using purified GBP-AP, trypsin was inactivated with 1 mM phenylmethylsulfonyl fluoride ("PMSF") rather than with calf serum.

The biosensor did not respond significantly to non-specific proteins as further demonstrated by the analyzes of relatively high concentrations of bovine serum albumin (BSA) or fluorescyl-labeled BSA. Some analyzes were done in the presence of 1 mg of BSA/ml to provide "carrier" protein, thereby minimizing the possibility of non-specific binding of antibodies and other proteins in dilute solutions.

Further evidence of the specificity of the biosensor response was obtained by demonstrating that anti-fluorescyl antibodies bound to the sensor surface were slowly released in the presence of 5 mm fluorescein-HCl at pH 8.0. Also, the binding of anti-fluorescyl antibody 72 to the sensor surface was inhibited when the antibody 72 was incubated in a solution of 1 mM fluorescein-HCl at pH 8.0 for 15 min prior to sampling in the biosensor.

The range of biosensor response and sensitivity to different concentrations of anti-fluorescyl antibody 72 were determined. The lowest concentration of antibody 72 detected by the biosensor two weeks after its construction was 0.33 nM (with a response that was double that of the background noise). Increasing concentrations of antibody 72 resulted in more rapid binding and greater changes in the apparent index of refraction at the biosensor surface.

IV. Universal Biosensor Using Protein A

Sequential binding was demonstrated by binding anti-fluorescyl antibodies to fluorescyl groups on the biosensor surface. Protein A, 52, was then bound to the Fc region of the antibodies 72 on the sensor surface and, in turn, anti-alkaline phosphatase antibodies were attached to the protein A, 52. A control study was conducted substituting the intact anti-fluorescyl antibody 72 with Fabs of anti-fluorescyl antibody 72 lacking the Fc region needed for Protein A 52 binding. Normal specific protein-protein interactions occurred at the biosensor surface. The ordered layering described above for the biomolecules on the gold surface 24 can be detected by the biosensor. Also, the binding of Fab (50 kDa) to fluorescyl groups resulted in a smaller biosensor response compared to that of intact antibody 72 (150 kDa).

Multifunctionality and changeability of specificity were demonstrated by attaching Protein A 52 covalently to the activated carboxyl groups on the GBP on the biosensor surface on which fluorescyl groups were already present. This resulted in a bifunctional biosensor with 2 distinct recognition elements, i.e., the fluorescyl antigen target and Protein A 52 that specifically binds to the Fc region of antibodies bound by Protein A 52. Alternatively, Protein G can be used to more specifically bind antibodies of the IgG class. The newly constructed biosensor responded independently by first detecting the binding of alkaline phosphatase to anti-alkaline phosphatase antibody 72 and, finally the binding of Fabs of anti-fluorescyl antibody 72 to fluorescyl targets on the biosensor.

Importantly, biosensors produced using the biosensor constructed with an alkanethiol (HS-$(CH_2)_{10}$-COOH) monolayer to anchor anti-fluorescyl antibodies to the gold surface 24 failed to achieve results comparable to those achieved using the apparatus and method of the present invention. The biosensor constructed by binding the specific recognition element using conventional techniques responded to the binding of fluorescyl-labeled bovine serum albumin. Its use for a second analysis was successful, however, even in its second use a diminished response was detected at the biosensor surface after regeneration with in 0.1 M Glycine-HCl buffer pH 2.5. A third analysis failed to produce a response, indicating that the recognition element was no longer on the gold surface 24. In the present study, the two GBP-biosensors constructed were stable for one month of daily use in solutions varying considerably in salt and detergent concentration and pH. The gold-binding polypeptide can also be used to both provide and stabilize biofilms on the gold surface 24 of other SPR sensors.

The presence of the GBP on the biosensor's gold surface 24 appeared to effectively block non-specific binding of proteins such as serum albumin and antibodies that are known to kind strongly to gold. Therefore, the method of coating a gold SPR-biosensor surface of the present invention can be used as a blocking agent following the construction of SPR-biosensors of the present invention, when using existing alkanethiol chemistry or whenever gold surfaces 24 need to be coated with a blocking agent.

The method of using a GBP to coat the surface of a gold SPR-biosensor of the present invention also has additional properties that make it well suited for biosensor construction. First, there was no need to introduce a hydrogel layer to provide a hydrophilic environment at the gold surface 24 as is the case with most sensors constructed with alkanethiol monolayers. The polar GBP appears to establish an aqueous environment allowing proteins to approach the gold surface 24 and interact normally with the recognition elements. Second, the GBP molecule provides several different and multiple reactive sites including amino, carboxyl and hydroxyl groups to which different recognition elements can be covalently attached. Finally, the observation that the reconstructed GBP-AP, unlike the original fusion protein, on a gold surface 24 was highly resistant to cleavage by trypsin suggests GBP-recognition element constructs made as described herein could be significantly more stable to proteolysis than analogous fusion proteins produced by genetic engineering methods.

The apparatus and method of the present invention have general implications for use with fusion proteins in constructing biosensors. Polypeptide stretches linking the functional domains of fusion partners are likely to be more susceptible to any proteases present in biological samples than are peptide bonds within domains. The GBP-AP used in this study has one or more protease susceptible bonds between the major GBP and AP domains. When the reconstructed molecule of the GBP and AP was prepared it was highly unlikely that the original peptide bond was formed as a significant percentage of the total reconstructed adducts. More likely, amide bonds were formed between the activated carboxyl groups(s) of the GBP and available epsilon amino groups of lysyl residues located on the surface of the alkaline phosphatase molecule. Amide bonds of this type are hydrolyzed at a slower rate by proteases than are normal peptide bonds. Also, globular proteins attached to the GBP in this manner are likely to block the access of proteases to susceptible bonds.

The GBP-biosensors of the present invention, and those constructed as taught herein, are highly reliable and gave a more consistent readout when the fluorescyl group recognition element was attached to the sensor surface and anti-fluorescyl antibody 72 was the analyte than when anti-alkaline phosphatase bound to Protein A 52 was the recognition element and alkaline phosphatase was the analyte. The binding of antibody 72 molecules (150 kDa) to the relatively small (370 Da) fluorescyl group close to the sensor's surface elicits a greater response, i.e., change in density near the sensor surface, than that produced when alkaline phosphatase (100 kDa) binds to antibody 72 attached to Protein A 52 at a greater distance away from the sensor's surface.

Therefore, the GBP-biosensor of the present invention, and those constructed in accordance with the methods of the present invention, even those that are a relatively small target, e.g., antigenic peptides, haptens or ligands on the surface that interact with large analytes such as antibodies or cellular receptors, are more sensitive than those produced using conventional methods. The enhanced sensitivity of the GBP-biosensors of the present invention was detected even in the presence of low concentrations of analytes. Furthermore, relatively small molecules were attached to the gold sensor surface at higher density than that of large proteins, thereby producing biosensors with a higher operating sensitivity.

The demonstration that Protein A 52 attached covalently to the GBP on the sensor surface could bind anti-alkaline phosphatase antibody 72 which in turn could bind alkaline phosphatase indicates that a single biosensor constructed with Protein A 52 on the surface is both versatile and convertible, so that the sensor's specificity can be changed simply by adding antibodies with the desired specificity.

EXAMPLE I

PREPARATION AND USE OF THE GBP-BIOSENSOR

Cell Culture and Preparation of Osmotic Shock Fluid

As thought by Brown, *E. coli* cell lines expressing pSB3053 and pSB2991 were cultured in YT broth at 34° C. See *Brown*, 1997. To prepare osmotic shock fluid (OSF) the cultured cells were collected by centrifugation at 3000×g for 15 min. Cells were resuspended in 0.3 M Tris-HCl buffer pH 8.0 containing 20% sucrose and 1 uM EDTA (TSE buffer) at room temperature in a volume equal to one-third of the original culture volume. The cells were collected by centrifugation at 5000×g for 15 min and resuspended in a volume of TSE buffer equal to 1/60th of the original culture volume. The resuspended cells were cooled to 4° C. and quickly added to a volume of 0.5 mM $MgCl_2$ equal to one-third of the original culture volume at 4° C. The cells were stirred for 10 min at 4° C. and then centrifuged at 4000×g for 15 min. The supernatant fluid (osmotic shock fluid) was recovered and refrigerated for later use.

Alkaline Phosphatase Assay

The activity of alkaline phosphatase and its chimeric form in osmotic shock fluid was determined by adding an appropriate volume (10 to 100 ul) to a sufficient volume of 5.5 mm p-nitrophenyl phosphate (pNPP) (Sigma) in 50 mM Tris-HCl buffer pH 8.0 (AP substrate) to a final volume of 1 ml. The change in absorbance at 405 nm was recorded over 15 to 60 minutes at room temperature.

Purification of Anti-fluorescyl Antibody and the GBP-AP

Mouse ascites fluid (2 ml) containing the monoclonal anti-fluorescyl antibody 72 (4.4.20) was diluted 1:5 in phosphate buffered saline, pH 7.4 containing 0.05% Tween 20 (PBS-T). The solution was centrifuged at 15,000×g for 15 min and passed through a 0.2 $\mu$M filter (Millipore Corp). The antibody 72 solution was passed over a 2 ml column of fluorescyl-Sepharose, the column rinsed with 25 ml of PBS-T and the antibody 72 eluted from the column in 0.1 M Glycine-HCl buffer, pH 2.1. Fractions (1 ml) were collected in tubes containing 150 ul 1 M Tris-HCl buffer, pH 8.0, and based on the absorbance at 280 nm those fractions containing antibody 72 were pooled and passed over a column of PD-10 (Pharmacia) equilibrated in PBS.

Osmotic shock fluid (OSF) containing the GBP-AP was supplemented with sodium chloride, Tris-HCl buffer, pH 8.0, and Tween 20 to final concentrations of 0.15 M, 50 mM and 0.05% (w/w), respectively, and then passed through a 0.2 $\mu$m filter. The filtered solution (100 to 200 ml) was passed over a column (2 ml) of cross-linked bis-acrylamide azlactone copolymer (Ultralink Biosupport from Pierce) that had rabbit anti- (*E. coli*) alkaline phosphatase (Harlan Sera-Lab) covalently attached to the support matrix (10 mg of antibody/ml of matrix). The column effluent solution was devoid of AP activity. The column was rinsed with 25 ml of 50 mm Tris-HCl buffer pH 8.0 containing 0.15 M sodium chloride and 0.05% Tween 20 (TBS-T) and the protein was eluded from the column in 0.1 M Glycine-HCl buffer pH 2.1, into tubes containing 150 $\mu$l of 1 M Tris-HCl buffer pH 8.0 Fractions with AP activity were pooled and concentrated while changing the buffer to PBS on a Ultrafree Biomax-10K centrifugal filter device (Millipore Corp). Protein concentrations were determined using the bicinchoninic acid (Pierce) procedure with bovine serum albumin as the standard.

Attachment of Fluorescyl Groups to Proteins

Ten milligrams of bovine serum albumin and 300 $\mu$grams of calf intestine alkaline phosphatase (Boehringer Mannheim) were labeled with fluorescyl groups by incubating the proteins in 2.5 ml of a solution of 2 mM fluorescein isothiocyanate (FITC) in 0.1 M sodium carbonate buffer pH 9.5 for 3 h at room temperature in the dark. Excess reagent was removed by passing the solution over a PD-10 column equilibrated in PBS. Fluorescyl-labeled proteins were stored in the dark in a refrigerator.

Binding of Chimeric GBP-AP to Gold

The GBP-AP in osmotic shock fluid (OSF) was bound to 2 mg of spherical gold powder with an average particle size of 1.5 $\mu$m (Aldrich Chemicals).

Glass microscope slides were prepared with a 100 nm layer of gold deposited over 2 nm layer of chromium in an electron-beam evaporator. The GBP-AP was bound to the gold-coated slides by layering 2 ml of a 2:15 dilution of OSF in 10 mM potassium phosphate buffer, pH 7.0, containing 100 mM potassium chloride and 1% Triton X-100 (PKT buffer) for 1 hour at room temperature. The slides were rinsed in PKT buffer and 50 mM Tris-HCl buffer pH 8.0 and assayed for alkaline phosphatase (AP) activity by overlayering 2 ml of AP substrate on the slides. The optimum binding of GBP-AP in dilutions of OSF to gold occurred in the presence of at least 50 mM potassium chloride. In contrast, the binding of immunopurified GBP-AP was most efficient in the presence of approximately 10 mM potassium chloride. The binding of the immunopurified GBP-AP was significantly inhibited as the salt concentration was increased.

Attachment of Recognition Elements to the GBP on Gold

The chemical procedures used to construct biosensors were developed first on gold-coated microscope slides. The GBP-AP on gold was cleaved by 10 $\mu$g of bovine trypsin (Sigma) per ml in 50 mM Tris-HCl buffer pH 8.0 (TB) continuing 0.1 m $CaCl_2$. Slides were rinsed in TB, incubated in 5% calf serum in TB for 30 min and then rinsed in TB. The carboxyl groups(s) in the GBP on gold were converted to reactive esters in a reaction with 10 mM 1-ethyl-3-(3-dimethyl-aminopropyl)-carbodiimide (EDC) and 2.5 mM-hydroxysulfosuccinimide (S-NHS), both from Pierce. Antibodies 72, alkaline phosphatase (Boehringer Mannheim) or Protein A 52 (Pierce) were then coupled to the GBP.

The slides were rinsed and stored in TB. Control slides were prepared either by omitting the carbodiimide reaction thereby preventing the attachment of protein to the GBP, activating the carboxyl groups and blocking them with ethanolamine before adding protein or by substituting non-specific antibodies that do not bind the target analyte 72, e.g. anti-fluorescyl antibodies with antibodies expected to not bind fluorescyl groups. Other gold-coated slides with the GBP on the surface were used to attach fluorescyl groups at available reactive amino groups in a reaction in 2 mM FITC in 0.1 M sodium carbonate buffer pH 9.5 for 3 hours at room temperature. The presence or absence of functional anti-fluorescyl antibody 72 attached to the GBP-gold slides was detected by determining if fluorescyl-labelled alkaline phosphatase would bind to the antibody 72 as ascertained by measuring AP activity. The presence of functional protein A 52 on the GBP-gold slides was determined by the capacity of the biofilm to find anti-fluorescyl antibody 72 which in turn could bind fluorescyl-labelled alkaline phophatase and assayed for AP activity. Slides with fluorescyl groups attached to the GBP were incubated with mouse anti-fluorescyl antibody 72. Bound antibody 72 was detected with anti-mouse IgG antibody 72 conjugated with alkaline phosphatase (Sigma). Reconstructed adducts of alkaline phosphatase chemically linked to the GBP domain on the gold surface were stable to digestion with a relatively high concentration (100 $\mu$g/ml) of trypsin at pH 8.0 for 2 h at room temperature demonstrating the robustress of chemical linkage to the peptide foundation as opposed to geneticlaly engineered peptide linages.

Construction and Use of Biosensors

The chemical procedures developed on gold-coated microscope slides to attach proteins and fluorescyl groups to the gold surface 24 were used to construct biosensors with the Texas Instruments miniature SPR system (TI-SPR). A removable flow cell (approximately 50 $\mu$l volume), constructed of teflon and Delrin, was designed to restrict to flow of reagents and solutions over the region (4.5 mm×0.025 mm) of the sensor surface producing the SPR signal. This concentrated the desired chemistry and sampling to a finite area on the gold surface 24, thereby conserving valuable reagents and samples. Also, a continuous stream of solutions of known concentrations was maintained over the sensor surface at a constant flow rate. Flow rates as low as 10 $\mu$l per minute were attained with a peristaltic pump.

PKT buffer (and all subsequent solutions) was pumped through the flow cell for 15 min at a flow rate of 40 $\mu$l/min at room temperature, followed by 20 $\mu$g of GBP-AP per ml of PKT buffer for 1 hour (1 ml total volume). The sensor surface was rinsed with PKT buffer and then incubated with 10 $\mu$g of trypsin per ml of 50 mM Tris-HCl buffer pH 8.0 for 30 min. Trypsin was removed by rinsing the sensor with TB for 15 min and any remaining trypsin was inactivated with freshly prepared 1 mM phenylmethylsulfonyl fluoride (PMSF) in TB for 30 min or with 5% calf serum in TB. Fluorescyl groups were attached to the GBP on the sensor surface by pumping a solution of 2 mM FITC in 0.1 M sodium carbonate buffer pH 9.5 through the flow cell for 3 hours at room temperature. Excess FITC was removed by rinsing the sensor with 0.1 M carbonate buffer pH 9.5 for 30 min and then with TB for 30 min. Protein A 52 was attached to the sensor surface using the carbodiimide attachment procedure as previously described. Solutions of analytes were sampled by pumping them through the flow cell for a minimum of 15 minutes followed by a rinse step for at least 15 min with 50 mM Tris-HCl pH 8.0 containing 0.1% Tween 20.

In operation, the GBP-biosensor of the present invention was used to detect the binding of mouse monoclonal anti-fluorescyl antibody 72 (4.4.20) to fluorescyl-labeled GBP on a biosensor surface (●) as shown in the graph in FIG. 4. A control antibody 72 preparation (○) consisted of the IgG fraction of rabbit polyclonal antiserum to *E. coli* alkaline phosphatase. A 50 μl flow cell was attached to the biosensor and solutions were pumped through at a flow rate of 40 μl/min at room temperature. The solutions, changed at times indicated by arrow head (▼), were: solution 1: 50 mM Tris-HCl buffer pH 8.0 containing 0.1% Tween 20 (TT buffer); solution 2: 100 nM antibody 72 in TT buffer. Binding of antibodies to the sensor surface was directly measured in real-time as an increase in the index of refraction at the surface over time. To make comparisons easier, the index of refraction baselines in solution 1 were adjusted slightly to superimpose the starting points of each analysis.

Figure 5:
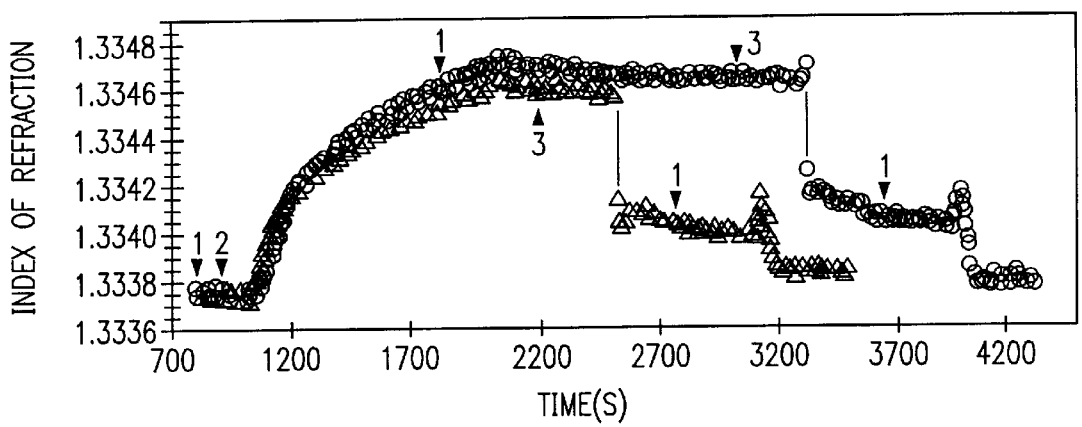
FIG. 5 demonstrates the relative stability of the biosensor according to one embodiment of the present invention.

FIG. 5 is a graph demonstrating the relative stability and reproducibility of a biosensor with fluorescyl-labeled GBP on its surface. The solutions used in the present study were: solution 1: TT buffer; solution 2, 100 nM anti-fluorescyl antibody 72 in TT buffer; solution 3: 0.1 M glycine-HCl buffer pH 2.1. The procedures were the same as those described in FIG. 4. Analysis 1 (●) was done one week after the sensor was constructed. Analysis 2 (○) was done 16 days later. The small differences (<10%) in the amount of antibody 72 binding between the 2 analyzes could be due to pipetting differences in preparing the antibody 72 solutions on separate days.

Figure 6:
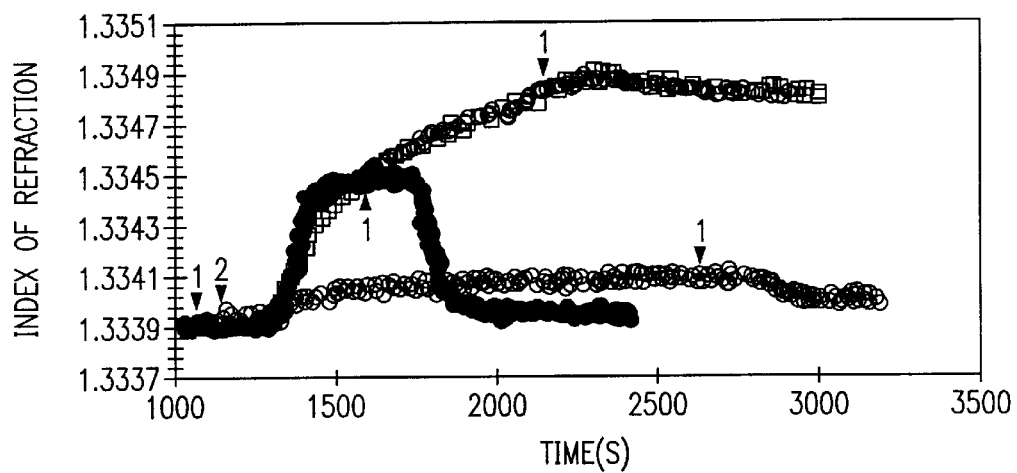
FIG. 6 is a chart demonstrating the index of refraction of a biosensor versus time illustrating that the biosensor does not react non-specifically to other proteins or molecules.

FIG. 6 is a graph demonstrating that the biosensor constructed with fluorescyl-labeled GBP on its surface does not respond significantly to non-specific proteins. Responses of the biosensor to 100 nM anti-fluorescyl antibody 72 (●), 16 μM bovine serum albumin (○) and 45 μM fluorescyl-labeled bovine serum albumin (□). The solutions used in this study were: solution 1: TT buffer; solution 2: protein solutions in TT buffer. The sampling of anti-fluorescyl antibody 72 was done immediately after those of the non-specific proteins.

Figure 7:
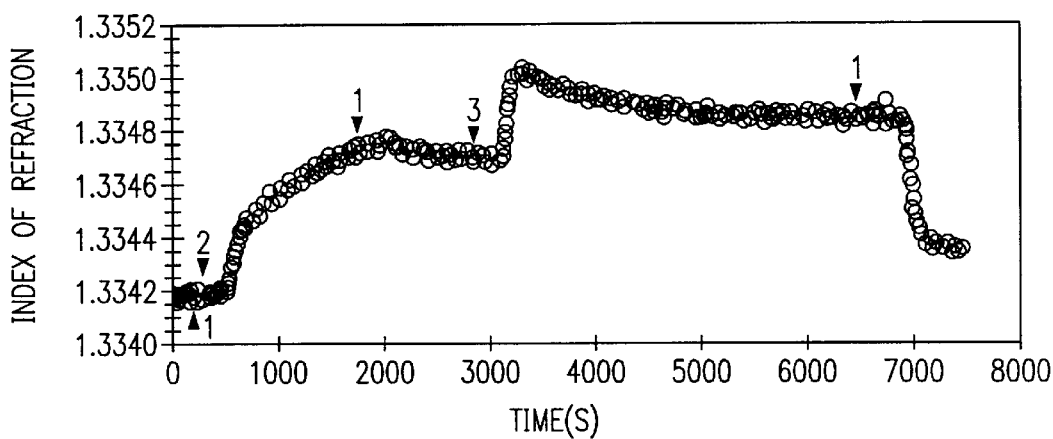
FIG. 7 shows the specific displacement of anti-fluorescyl antibodies bound to the biosensor of the present invention.

FIG. 7 is a graph demonstrating the specific displacement of anti-fluorescyl antibodies bound to a biosensor with fluorescyl-labeled GBP on its surface in the presence of fluorescein-HCl. In this study the solutions used were: solution 1: TT buffer; solution 2: 100 nM anti-fluorescyl antibody 72 in TT buffer; solution 3: 5 mM fluorescein-HCl in TT buffer.

Figure 8:
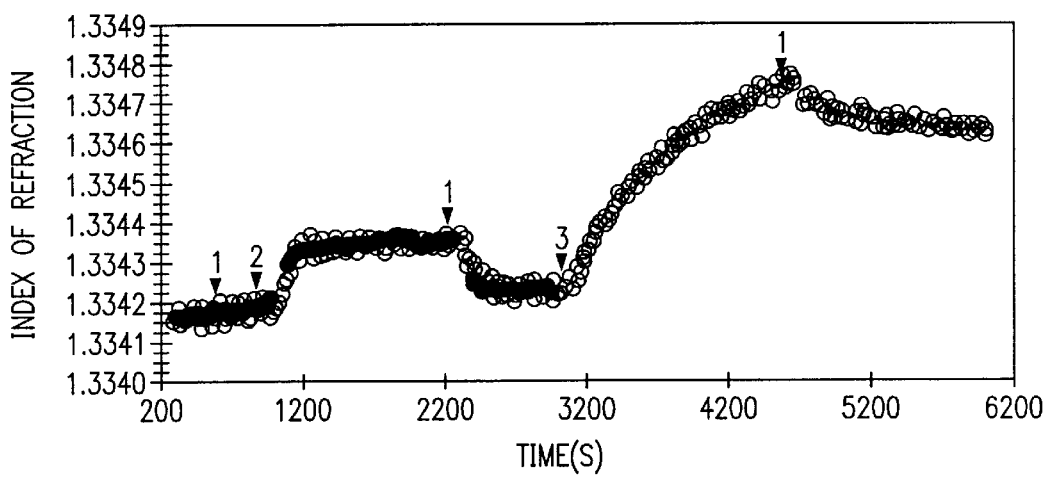
FIG. 8 demonstrates that the binding of anti-fluorescyl antibodies can be inhibited by preincubating the antibody with antigen(fluorescein—HCL)

FIG. 8 is a graph that demonstrates that the binding of anti-fluorescyl antibody 72 to fluorescyl-labeled GBP on the biosensor surface was inhibited by preincubating the antibody 72 in fluorescein-HCl. In this study the solutions used were: solution 1: TT buffer; solution 2: 100 nM anti-fluorescyl antibody 72 in the presence of 1 mM fluorescein-HCl in TT buffer; solution 3: 100 nM anti-fluorescyl antibody 72 in TT buffer. Solution 2 was incubated for 15 min prior to sampling in the biosensor. The results indicate that 1 mM fluorescein inhibited the binding of anti-fluorescyl antibody 72 and that the biosensor responded as expected to anti-fluorescyl antibody 72 in the absence of fluorescein-HCl.

Figure 9:
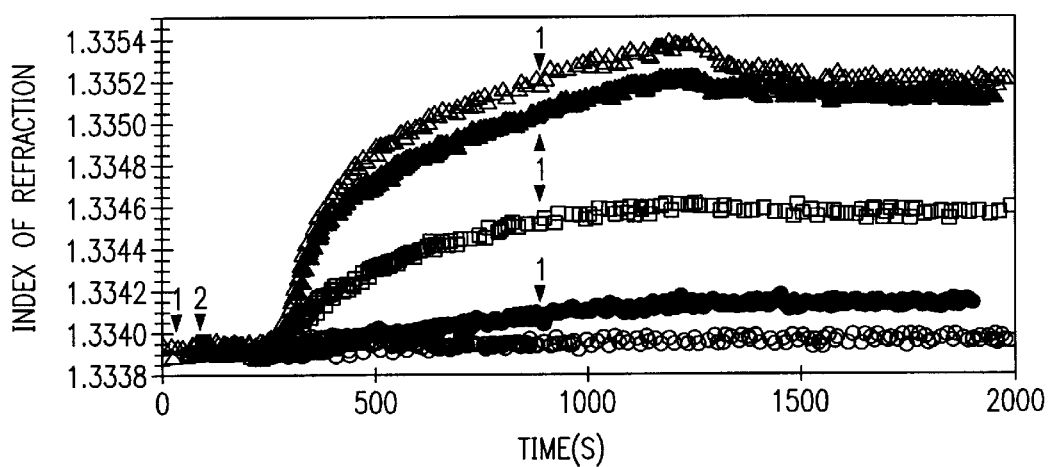
FIG. 9 shows the concentration dependence of specific binding of anti-fluorescyl antibodies to the surface of the sensor with fluorescein as a target.

FIG. 9 shows the response of the biosensor to increasing concentrations of anti-fluorescyl antibodies. Binding of antibody 72 to fluorescyl-labeled GBP on the sensor surface occurred during 15 min of sampling at a constant flow rate of 40 μl/min. Analyzes were all done on the same day proceeding from low to higher antibody 72 concentration. The biosensor was regenerated with 0.1 M Glycine-HCl buffer pH 2.1 after each analysis. The solutions used in the present study were: solution 1: TT buffer; solution 2: antibody 72 in TT buffer. Antibody 72 concentrations were: 0.67 nM (○); 3.4 nM (●); 34 nM (□); 340 nM (■); 680 nM (Δ). The results indicated that the initial rate of antibody 72 binding to the fluorescyl target accelerated as the antibody 72 concentration was increased and that binding in the presence of 680 nM antibody 72 appeared to approach the maximum response of this biosensor.

Figure 10:
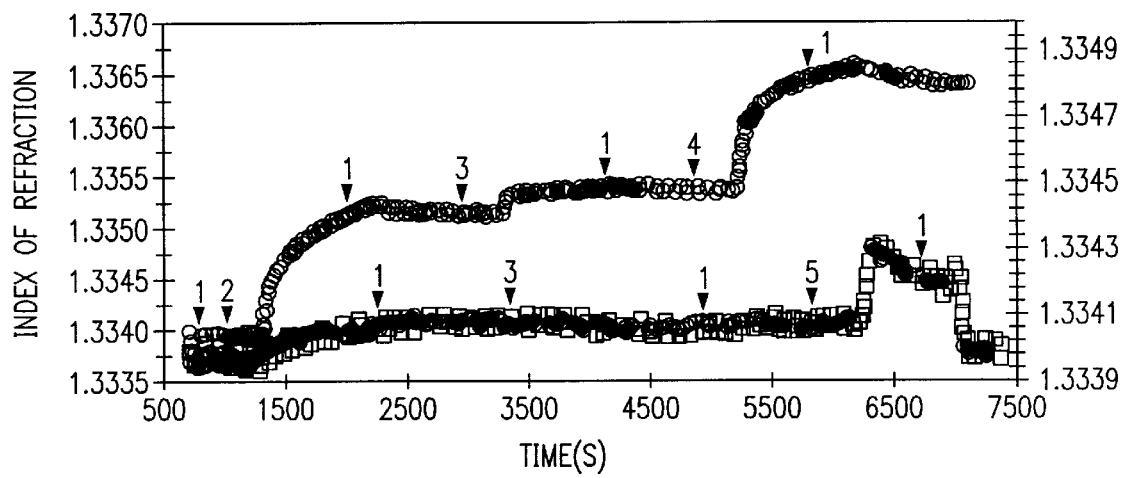
FIG. 10 shows the response of a protein A-based convertible biosensor.

The graph in FIG. 10 demonstrates that Protein A 52 binds to anti-fluorescyl antibody 72 that was bound to fluorescyl-labeled GBP on the surface of the biosensor of the present invention (○). The Fab preparation of anti-fluorescyl antibody 72 lacking an Fc region bound to the sensor surface (index of refraction scale on the right), but did not bind Protein A 52 (□). The solutions used in the present study were: solutions: 1, TT buffer; 2, 340 nM anti-fluorescyl antibody 72 or 300 nM Fab preparation of anti-fluorescyl antibody 72 in TT buffer; 3, 1.3 μM Protein A 52 in TT buffer; 4, 340 nM anti-alkaline phosphatase in TT buffer; 5, 0.1 M Glycine-HCl buffer pH 2.1.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method of immobilizing a molecule to a gold surface comprising the steps of:

attaching to he gold surface a gold binding polypeptide-alkaline phosphatase chimera, wherein the gold binding polypeptide comprises the amino acid sequence MHGKTQATSGNQS (SEQ ID NO.: 1) in a repeated peptide structure;

cleaving the alkaline phosphatase domain off the chimera after attaching the chimera to the gold surface to provide a surface-bound protease-resistant gold binding polypeptide domain comprising the repeated amino acid sequence of SEQ ID NO.: 1; and binding the molecule to said surface-bound gold binding polypeptide via a proteolysis-resistant linkage.

2. The method of claim 1, wherein said gold binding polypeptide is a synthetically constructed repeated polypeptide structure.

3. The method of claim 1, further comprising the step of blocking said gold surface with said gold binding polypeptide to coat said gold surface and act as a blocking agent.

4. The method of claim 1, wherein said molecule attached to said gold binding polypeptide is Protein A.

5. The method of claim 1, wherein said molecule attached to said gold binding polypeptide is an antibody.

6. A sensor surface made in accordance with the method of claim 1.

7. A method of coating a gold surface comprising the steps of:

attaching a polypeptide comprising the amino acid sequence MHGTQATSGTIQS (SEQ ID NO: 1) to the gold surface; and covalently binding a recognition element to said polypeptide via a proteolysis-resistant linkage.

8. The method of claim 7, wherein said polypeptide is isolated prior to attaching to the gold surface.

9. The method of claim 7, wherein said polypeptide is a synthetic polypeptide.

10. The method of claim 7, wherein said polypeptide is used as a blocking agent to coat said gold surface.

11. The method of claim 7, wherein said molecule attached to said polypeptide is Protein A.

12. The method of claim 7, wherein said molecule attached to said polypeptide is Protein G.

13. The method of claim 7, wherein said peptide is further defined as being attached to a protein by a protease resistant covalent linker.

14. The method of claim 7, wherein said polypeptide is further defined as comprising a polynucleotide that has been covalently attached to the polypeptide.

15. The method of claim 7, wherein said polypeptide is further defined as comprising an biotin molecule covalently bound to the polypeptide.

16. The method of claim 7, wherein said gold surface is further defined as comprising a portion of a sensor surface.

17. The method of claim 16, wherein said sensor surface is part of a surface plasmon resonance sensor.

18. The method of claim 7, whercei said polypeptide is obtained by the steps of:

expressing a peptide library;

binding said peptide library to gold; and identifyiing the clones from said peptide library that express a polypeptide that binds specifically to gold.

19. The method of claim 7, further comprising the step of binding covalently the peptide to the molecule using a bivalent cross-linking molecule.

\* \* \* \* \*